United States Patent
Lin

(10) Patent No.: US 12,150,779 B2
(45) Date of Patent: Nov. 26, 2024

(54) TERAHERTZ FIELD EFFECT NON-INVASIVE BIOFEEDBACK DIAGNOSIS SYSTEM

(71) Applicant: Chien-Feng Lin, Shenzhen (CN)

(72) Inventor: Chien-Feng Lin, Shenzhen (CN)

( * ) Notice: Subject to any disclaimer, the term of this patent is extended or adjusted under 35 U.S.C. 154(b) by 632 days.

(21) Appl. No.: 17/114,412

(22) Filed: Dec. 7, 2020

(65) Prior Publication Data

US 2022/0175308 A1    Jun. 9, 2022

(51) Int. Cl.
*A61B 5/00* (2006.01)

(52) U.S. Cl.
CPC .............. *A61B 5/486* (2013.01); *A61B 5/002* (2013.01); *A61B 5/0048* (2013.01); *A61B 5/7217* (2013.01)

(58) Field of Classification Search
CPC ....... A61B 5/486; A61B 5/0048; A61B 5/002; A61B 5/7217
See application file for complete search history.

(56) References Cited

U.S. PATENT DOCUMENTS

| | | | |
|---|---|---|---|
| 4,031,883 A | 6/1977 | Fehmi et al. | |
| 4,195,626 A * | 4/1980 | Schweizer | A61B 5/377 600/587 |
| 4,690,142 A | 9/1987 | Ross et al. | |
| 4,800,893 A | 1/1989 | Ross et al. | |
| 4,928,704 A * | 5/1990 | Hardt | A61B 5/375 600/545 |
| 4,940,060 A * | 7/1990 | Gu | A61H 39/02 600/548 |
| 4,951,674 A | 8/1990 | Zanakis et al. | |
| 5,108,361 A | 4/1992 | Hein | |
| 5,365,939 A | 11/1994 | Ochs | |
| 5,392,788 A | 2/1995 | Hudspeth | |
| 5,458,142 A | 10/1995 | Farmer et al. | |
| 5,769,878 A | 6/1998 | Kamei | |

(Continued)

FOREIGN PATENT DOCUMENTS

| | | | | |
|---|---|---|---|---|
| JP | 2005315708 A | * | 11/2005 | ......... G01N 21/3563 |
| KR | 20090023191 A | * | 8/2008 | ............... H01S 1/02 |
| WO | WO-2016048257 A1 | * | 3/2016 | ............. G01N 22/00 |

OTHER PUBLICATIONS

English Translation of JP-2005315708-A (Year: 2005).*
English Translation of KR-20090023191-A (Year: 2009).*

*Primary Examiner* — Christopher Koharski
*Assistant Examiner* — Helene Bor

(57) ABSTRACT

A terahertz field effect non-invasive biofeedback diagnosis system comprises a trigger sensor, a terahertz wave source field unit, and a central processing & telemetry unit. The central processing and telemetry unit (CP&T) is used to generate different types of stimulus signals to patients and system operation units. The biofeedback diagnosis system is used to form two biofeedback loops: one loop is through a CP&T-patient-trigger sensor loop and the other loop is through a CP&T-operation unit-trigger sensor loop. The trigger sensor can remotely obtain the biofeedback signal of the patient, and process the feedback signal into a digital signal and send it back to the central processing and telemetry unit. In order to improve the feedback signal of patients, the terahertz wave source field unit is placed near the patient, so as to trigger the feedback signals of biological cells, tissues, organs and brain waves of patients for diagnosis.

9 Claims, 7 Drawing Sheets

(56) References Cited

U.S. PATENT DOCUMENTS

| | | | |
|---|---|---|---|
| 5,983,129 A | 11/1999 | Cowan et al. | |
| 6,097,981 A | 8/2000 | Freer | |
| 6,292,688 B1* | 9/2001 | Patton | A61B 5/378 |
| | | | 600/545 |
| 2003/0069513 A1* | 4/2003 | Nesterov | A61B 5/377 |
| | | | 600/545 |
| 2004/0077960 A1* | 4/2004 | Tanaka | A61B 5/486 |
| | | | 600/504 |
| 2008/0114417 A1* | 5/2008 | Leyde | A61N 1/36082 |
| | | | 607/60 |
| 2009/0082691 A1* | 3/2009 | Denison | A61B 5/374 |
| | | | 600/544 |
| 2010/0081959 A1* | 4/2010 | Nesterov | A61B 5/6838 |
| | | | 600/544 |
| 2014/0081348 A1* | 3/2014 | Fischell | A61N 1/36071 |
| | | | 607/45 |
| 2017/0370834 A1* | 12/2017 | Kassab | G01J 3/10 |

* cited by examiner

TERAHERTZ FIELD EFFECT NON-INVASIVE BIOFEEDBACK DIAGNOSIS SYSTEM

BACKGROUND OF THE INVENTION

1. Field of the Invention

The present disclosure relates to a biofeedback medical diagnosis system, and in particular to a terahertz field effect non-invasive biofeedback diagnosis system.

2. Description of the Related Art

A variety of medical diagnosis systems are known in the art to determine the general pathophysiological state of patients and diagnose various diseases. The visual diagnostic devices are based on critical fusion frequencies, such as Schweizer, U.S. Pat. No. 4,195,626, which describes a biofeedback device. It includes the application of various auditory, visual, electrical or tactile stimuli in specially designed biofeedback rooms. In addition, the rhythm patterns of these stimuli are controlled by microprocessors and adjusted according to the patient's own response.

In U.S. Pat. No. 4,690,142 of Ross et al., electrical nerve stimulation is recommended for specific parts of the patient's skin. The generation of this tactile stimulus to the skin is an electrical property used to produce the body's response to specific conditions. The system of the invention is also used to train the body to change the response to stimuli by concentrating on increasing or inhibiting touch.

In U.S. Pat. No. 4,031,883, a multichannel biofeedback computer is described by Fehmi et al. It includes some unipolar electrical contacts that are applied to the scalp and the patient's body, as well as a computer that collects, filters, and amplifies electrical signals. The overall feedback signal is then fed back to the patient to make the patient aware that the monitored function is being used for other purposes.

In U.S. Pat. No. 4,800,893, a kinesthetic physical motion display is described by Ross et al., in which multiple electrodes feed their respective signals to EEG devices equipped with video displays. The generation of kinesthetic body movements allows users to generate desired patterns of thinking.

In U.S. Pat. No. 5,365,939, Ochs describes a method of using EEG feedback to treat patients, which involves selecting a reference position for determining the frequency of brain waves and introducing it in two directions until a predetermined stop point is reached. Flexibility is then assessed according to the patient's ability to change the frequency of brain waves.

In U.S. Pat. No. 5,392,788, Hudspeth proposes a method and device for interpreting concepts and conceptual ideas from patients' brain wave data and helping to diagnose brain wave dysfunctions. A system is described, including a sensor for sending stimuli to patients, an EEG sensor for recording brain wave signals, and a computer for presenting control signals, recording and analyzing EEG signals. Compare recorded EEG signals with conceptual perception and emotional thinking models, or as a substitute for known EEG signals in healthy people to diagnose brain dysfunction.

In U.S. Pat. No. 5,983,129, Cowan et al. proposed a method for determining the intensity of focused attention, including obtaining frontal brain wave EEG signals and subtracting this signal from a separately obtained reference EEG signal to generate an attention indication signal.

Finally, Freer describes a biofeedback system based on an electroencephalograph, which maintains computer animations and presents it to patients while acquiring and analyzing electroencephalogram response signals in U.S. Pat. No. 6,097,981. The analysis results are then used to control the animation. The invention provides a device for sending an electroencephalogram signal from a patient's head or user to a machine by means of a remote infrared transmitter.

All of the above systems have some common limitations, which arise from their dependence on the patient's state of consciousness. Another limitation is that patients themselves are used to interpret biofeedback signals rather than independent operating entities like independent operators. Finally, the EEG signal is acquired by hardware and transmitted to the main data acquisition and calculation device by wired or infrared mode.

In the art, it is also known to use magnetic and electromagnetic fields to remotely and non-invasively assess certain conditions of a patient or to affect his state of fatigue and ability to perform specific functions. In U.S. Pat. No. 5,458,142, Farmer et al. described a device for monitoring magnetic fields produced by organisms. It includes a magnetic field sensor comprising a ferromagnetic core surrounded by thin multi-turn wires. The sensor is used to record the magnetic field of an organism, for diagnostic purposes, and to control the magnetic field generator to generate a therapeutic magnetic field complementary to the biological magnetic field.

In U.S. Pat. No. 4,951,674, Zanakis et al. describe a biomagnetic analysis system that includes many optical fiber magnetic sensors for obtaining information about magnetic fields from various tissues of the human body, including the brain.

In U.S. Pat. No. 5,108,361, Hein proposes a device that affects organisms, including exposing patients to several short pulses of increased or decreased frequency to stimulate brain waves.

In U.S. Pat. No. 5,769,878, Kamei proposed a non-invasive device to enhance human immune surveillance by providing pulsed light to his forehead (while shielding his eyes) at a frequency range of 0.5 to 13 Hz, preferably in the alpha band measured from EEG signals.

The technologies described in the aforementioned patents have some insurmountable disadvantages:
1) Biofeedback signals are susceptible to the influence of patients' subjective consciousness.
2) Biofeedback signals are susceptible to environmental and noise interference.
3) Biofeedback signals lack standard baseline points as a reference basis.
4) The biofeedback signal lacks the mechanism to strengthen the rotation and vibration signals of biomolecules, so that the feedback signal enhances the signal intensity, improves the detection sensitivity, and obtains more meaningful information from it.
5) The biofeedback signal lacks the analysis and comparison of frequency, phase, and time sequence, and cannot identify the position and frequency band of biomolecules to capture accuracy.

BRIEF SUMMARY OF THE INVENTION

Therefore, an object of the present invention is to overcome the bottlenecks and shortcomings of the prior art by providing a biofeedback diagnosis system that provides a series of stimulus signals to a patient and has a reference baseline standard point to collect valuable biofeedback signals.

Another object of the present invention is to provide a diagnosis system capable of processing two biofeedback loops from a patient and an operation unit. The reference standard point signal provided by the operation unit and the biofeedback signal of the patient loop are processed, analyzed and compared with the trigger sensor to obtain a more accurate signal.

Another object of the present invention is to provide a diagnosis system in which biofeedback from a patient is collected non-invasively.

To achieve the above purpose, the present invention provides a terahertz field effect non-invasive biofeedback diagnosis system, comprising: a central processing and telemetry unit; a trigger sensor, the trigger sensor being non-invasive and capable of noise processing; and a terahertz wave source field unit, coupled to the central processing and telemetry unit, and used for use in the terahertz electromagnetic spectrum for disease prevention. Rotation and vibration energy triggering of human biomolecules is utilized. The central processing and telemetry unit is used to generate a predetermined series of stimulus signals, and simultaneously transmit the stimulus signals to the operation unit and the patient, thereby forming a plurality of biofeedback loops.

The plurality of biofeedback loops comprises: a first biofeedback loop and a second biofeedback loop. The first biofeedback loop comprises the central processing and telemetry unit transmitting the stimulus signals to the patient, the trigger sensor being used for remotely detecting the biofeedback signal of the biomolecule of the patient, the trigger sensor further processing the biofeedback signal to obtain a processed feedback signal and sending the processed feedback signal back to the central processing and telemetry unit. The second biofeedback loop comprises the central processing and telemetry unit transmitting the stimulus signals to the operation unit, the operation unit converting the stimulus signals into a reference standard point signal, the trigger sensor receiving the reference standard point signal and sending it back to the central processing and telemetry unit simultaneously with the processed feedback signal. The second biofeedback loop creates a reference loop that provides a reference value for accurately calculating the phase and intensity of the processed feedback signal.

An embodiment of a terahertz field effect non-invasive biofeedback diagnosis system of the present invention, in which a terahertz wave source field unit (0.1-10 THz) device is provided to enhance a patient's feedback signal, terahertz electromagnetic spectrum and biological molecules (such as DNA, RNA, protein, etc.). Rotational and vibrational energy generation corresponds to trigger feedback signals such as patient biological cells, tissues, organs and brain waves for diagnostic purposes. In addition, for some biomolecules that are insensitive to terahertz field response under conventional conditions, a split-ring resonator (SRR) structure can be used to enhance the terahertz field local electromagnetic response to promote the sensitivity of biofeedback signals from patients to devices.

In some embodiments of a terahertz field effect non-invasive biofeedback diagnosis system, the central processing and telemetry unit comprises a stimulus signal generation module and a stimulus signal transmission device. The stimulus signal generation module is for generating the predetermined series of the stimulus signals. The stimulus signal transmission device is coupled to the stimulus signal generation module and used for simultaneously transmitting the stimulus signals to the operation unit and the patient.

In some embodiments of a terahertz field effect non-invasive biofeedback diagnosis system, the stimulus signals include at least one of a magnetic, electromagnetic, audio and visual stimulus signals, or a combination thereof.

In some embodiments of a terahertz field effect non-invasive biofeedback diagnosis system, the trigger sensor also includes a detector channel equipped with a logarithmic periodic antenna to enhance the reception of the biofeedback signal.

In some embodiments of the terahertz field effect non-invasive biofeedback diagnosis system, the logarithmic periodic antenna is a multi-turn conical helical antenna for receiving short waves in the range of 450 MHz to 6000 MHz.

In some embodiments of a terahertz field effect non-invasive biofeedback diagnosis system, the detector channel also comprises a mixer, a rectifier, a discriminator, and a heterodyne. The logarithmic periodic antenna is coupled to the mixer; the mixer is coupled to the rectifier, the discriminator, and the heterodyne; and the rectifier is coupled to the discriminator, thereby enhancing the reception of the biofeedback signal.

In some embodiments of a terahertz field effect non-invasive biofeedback diagnosis system, the trigger sensor also includes a sensing element, an integrator, a differential amplifier, an amplifier, and a comparator. The sensing element is coupled to the integrator and the differential amplifier; the differential amplifier is coupled to the amplifier; and the amplifier is coupled to the comparator, thereby enabling the trigger sensor to analyze and compare the frequency, phase and timing of the biofeedback signal.

In some embodiments of a terahertz field effect non-invasive biofeedback diagnosis system, the central processing and telemetry unit is used to initiate the terahertz wave source field unit (e.g., 0.1-10 THz), thereby triggering the rotation and vibration energy of the biomolecule of the patient using the terahertz electromagnetic spectrum, which can generate rotation and vibration of the corresponding biomolecule (such as DNA, RNA, protein, tissue and organ, etc.), thereby triggering the biomolecule feedback signal of the patient to generate corresponding variables.

In some embodiments of a terahertz field effect non-invasive biofeedback diagnosis system, the terahertz wave source field unit includes a split-ring resonator (SRR) structure to enhance the terahertz field local electromagnetic response, thereby enhancing the absorption sensitivity of the terahertz spectrum to various biomolecules.

In some embodiments of a terahertz field effect non-invasive biofeedback diagnosis system, the terahertz frequency band of the terahertz wave source field unit is between 0.1 and 10 THz.

In some embodiments of a terahertz field effect non-invasive biofeedback diagnosis system, the terahertz wave generation mode of the terahertz wave source field unit may be caused by: semiconductor instantaneous current generation, accelerated electron generation, photorectification generation, semiconductor photoconductivity generation, non-linear differential frequency generation, thermal radiation generation, high energy accelerator generation, thermal radiation generation, or Fourier transformation infrared spectrum generation.

For a better understanding of the features and technical contents of the present invention, please refer to the following detailed description and drawings of the present invention, but these descriptions and the attached drawings are only used to illustrate the present invention, not to limit the scope of the invention.

BRIEF DESCRIPTION OF THE DRAWINGS

In order to more clearly illustrate the embodiments of the present invention or the technical solutions in the prior art, the appended drawings to be used in the description of the embodiments will be briefly introduced below. Obviously, the appended drawings described below are only some embodiments of the present invention, and for those of ordinary skill in the art, other drawings can also be obtained based on these appended drawings without undue labor.

DETAILED DESCRIPTION OF THE INVENTION

To facilitate understanding of the object, characteristics and effects of this present disclosure, embodiments together with the attached drawings for the detailed description of the present disclosure are provided.

Figure 1A:
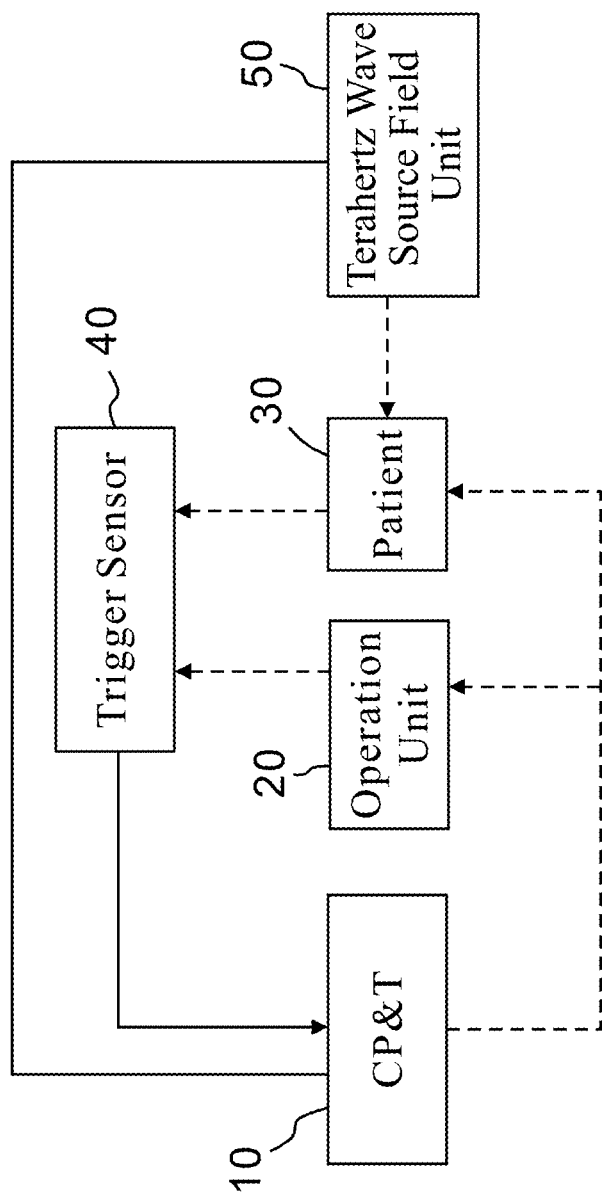
FIG. 1A is an application scenario schematic of an example of a terahertz field effect non-invasive biofeedback diagnosis system.

Refer to FIG. 1A. FIG. 1A is a schematic application scenario for an example of a terahertz field effect non-invasive biofeedback diagnosis system. As shown in FIG. 1, the terahertz field effect non-invasive biofeedback diagnosis system includes a central processing and telemetry unit (CP&T) 10, a trigger sensor 40, and a terahertz wave source field unit 50. The trigger sensor 40 is non-invasive and capable of noise processing. The terahertz wave source field unit 50 is electrically coupled with the central processing and telemetry unit 10 and is used to trigger the rotation and vibration energy of a patient's biomolecule using the terahertz electromagnetic spectrum.

The central processing and telemetry unit 10 is used to generate a predetermined series of stimulus signals and simultaneously transmit the stimulus signals to the operation unit 20 and the patient 30, and thus forms a plurality of biofeedback loops comprising: a first biofeedback loop and a second biofeedback loop.

The first biofeedback loop comprises the central processing and telemetry unit 10 sending the stimulus signals to the patient 30, the trigger sensor 40 being used for remotely detecting the biofeedback signal of the biomolecule of the patient 30, and the trigger sensor 40 further processing the biofeedback signal to obtain the processed feedback signal and sending the processed feedback signal back to the central processing and telemetry unit 10.

The second biofeedback loop comprises: the central processing and telemetry unit 10 transmitting the stimulus signals to the operation unit 20, the operation unit 20 converting the stimulus signals into a reference baseline standard point signal, the trigger sensor 40 receiving the reference baseline standard point signal and sending it back to the central processing and telemetry unit 10 simultaneously with the processed feedback signal to form a reference loop that provides a reference value for accurately calculating the phase and intensity of the feedback signal.

The reference baseline loop provides a reference value for accurately calculating the phase and intensity of the feedback signal. This refers to the net signal obtained by the first biofeedback loop minus the second biofeedback loop, and signals and phase amplifications are performed on this net signal. In detail, the difference between the second biofeedback loop and the first biofeedback loop is that in addition to the biofeedback signal of patient 30, the signal of the first biofeedback loop also includes the stimulus signals and the noise generated by the environment and equipment. The purpose of the second biofeedback loop is to collect the stimulus signals and the noise generated by the environment and equipment at the same time. The second biofeedback loop is for collecting the stimulus signals and the noise generated by the environment and equipment at the feedback loop as a reference signal. After subtracting the reference signal of the second biofeedback loop from the first biofeedback loop, it is beneficial to accurately amplify the phase and intensity of the feedback signal, so the biofeedback signal can be accurately obtained.

Figure 1B:
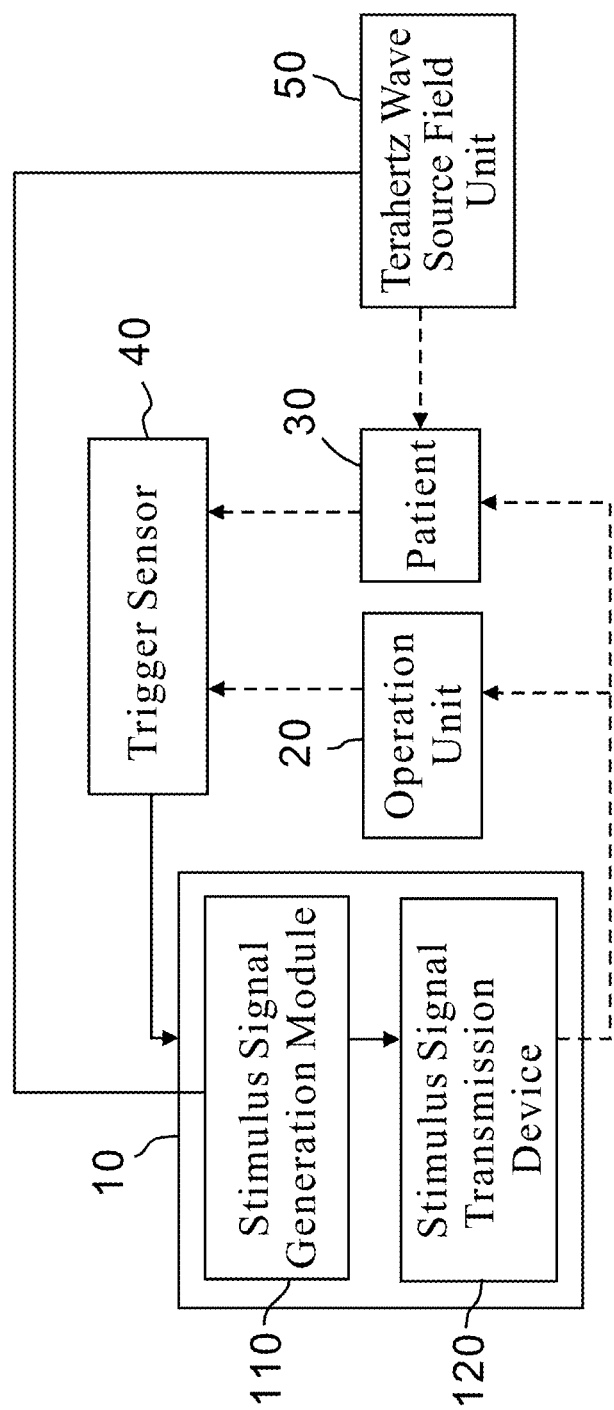
FIG. 1B is an application scenario schematic of another embodiment of a terahertz field effect non-invasive biofeedback diagnosis system.

Refer to FIG. 1B. FIG. 1B is an application scenario schematic of another embodiment of a terahertz field effect non-invasive biofeedback diagnosis system. As shown in FIG. 1B, the terahertz field effect non-invasive biofeedback diagnosis system is an architecture based on FIG. 1A, in which the central processing and telemetry unit 10 may include: a stimulus signal generation module 110 and a stimulus signal transmission device 120. The stimulus signal generation module 110 is used to generate the predetermined series of the stimulus signals. The stimulus signal transmission device 120 is coupled to the stimulus signal generation module 110 and is used for simultaneously transmitting the stimulus signals to the operation unit 20 and the patient 30. The stimulus signal transmission device 120 is an apparatus for connecting peripheral devices and transmitting the stimulus signals. For example, the central processing and telemetry unit 10 can be implemented based on microprocessors, microcontrollers, programmable circuits such as application specific integrated circuits (ASICs), field programmable gate arrays (FPGAs), or other control circuits or computing circuits, as well as computing devices, computer systems, etc. For example, the central processing and telemetry unit 10 controls the current, voltage, and frequency to generate stimulus signals, and generates a series of stimulus signals in the form or combination of electromagnetic waves, video, audio waves, or appropriate waves.

The central processing and telemetry unit 10 uses the stimulus signal generation module 110 to output a predetermined series of stimulus signals (also named as "information codes") and sends the series of stimulus signals to the operation unit 20 and the patient 30 through the stimulus signal transmission device 120 (the signal transmission path shown by the dashed lines in FIG. 1C). The operation unit 20 is used for forming a second biofeedback loop to generate a reference signal, and the operation unit 20 can be realized by using a circuit capable of collecting a stimulus signal, for example. The stimulus signal transmission device 120 may utilize, for example, a peripheral device to achieve transmission of the stimulus signal. Depending on the nature of the information code, the terahertz field effect non-invasive biofeedback diagnosis system can send stimulus signals using many appropriate peripherals. Examples of such peripheral devices include, but are not limited to, electromagnetic wave frequency generators, magnetic induction coils for modulating magnetic field transmission, headphones or speakers for audio transmission, video images, and light fields of various bands. It is noted that such information codes are simultaneously transmitted to the operation unit 20 and the patient 30, which is a unique feature of the diagnosis system of the present invention.

The trigger sensor 40 collects a reference baseline standard point signal (blank) from the operation unit 20 and a biofeedback signal from the patient 30 (as indicated by the dashed lines from the operation unit 20 and the patient 30 to the trigger sensor 40 in FIG. 1A or FIG. 1B), optimizes and processes them into a digital signal and sends it back to the central processing and telemetry unit 10 (as indicated in FIG. 1A or FIG. 1B by a solid line from the trigger sensor 40 to the central processing and telemetry unit 10). The following will provide examples for illustration in detail.

The terahertz wave source field unit 50 can be designed to operate directly with the patient 30. The terahertz electromagnetic spectrum corresponds to the rotation and vibration energy of biological molecules (such as DNA, RNA, protein, etc.) to enhance the generation of feedback signals triggering the patient's biological cells, tissues, organs and brain waves. The feedback signals are processed accurately by the trigger sensor 40 for diagnostic purposes. The terahertz frequency band of the terahertz wave source field unit 50 is preferably between (0.1-10 THz), however the present invention is not limited by this example. The terahertz wave source field unit 50 may be generated by at least one of the devices including: semiconductor instantaneous current generation, accelerated electronic generation, photorectification generation, semiconductor photoconductivity generation, non-linear differential frequency generation, thermal radiation generation, high energy accelerator generation, thermal radiation generation, and Fourier transform infrared spectroscopy generation. In order for some biomolecules to be insensitive to terahertz field response under conventional conditions, an open resonator (SRR) structure is more useful in some embodiments to enhance the terahertz field local electromagnetic response, thereby enhancing the sensitivity of terahertz spectroscopy to biomolecules.

The terahertz wave source field unit 50 is in collaboration with the central processing and telemetry unit 10. For example, when detecting different organs, the terahertz wave source field unit 50 can be used to generate different frequency band signals that transmit wave frequencies for the organ.

It mainly causes the vibration and rotation of organ protein molecules to generate specific biofeedback signals of the organ, and then analyze the signals for diagnosis.

For example, the central processing and telemetry unit 10 may be configured to control the turning on or off of the terahertz wave source field unit 50 by, for example, a control signal, or to instruct the terahertz wave source field unit 50 to generate different frequency band signals, thereby realizing the purposes of detecting biofeedback signals or detecting different organs.

Figure 2A:
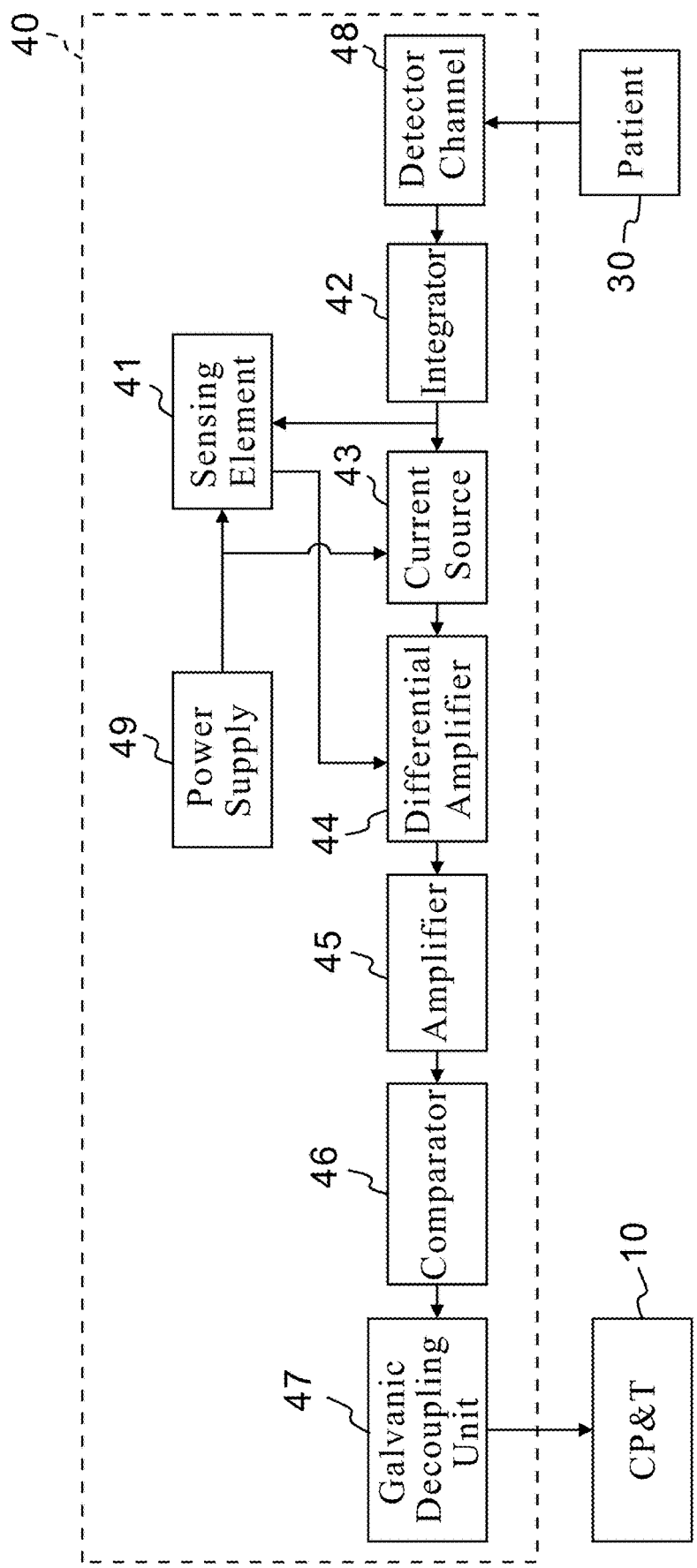
FIG. 2A is a block diagram of an embodiment of a trigger sensor.

Refer to FIG. 2A. FIG. 2A is a block diagram of an embodiment of a trigger sensor. The trigger sensor 40 includes a sensing element 41, an integrator 42, a current source of electrical current 43, a differential amplifier 44, an amplifier 45, a comparator 46, a galvanic decoupling unit 47, and a detector channel 48 for increasing the effect of patient feedback signals on the sensing element 41.

Figure 2B:
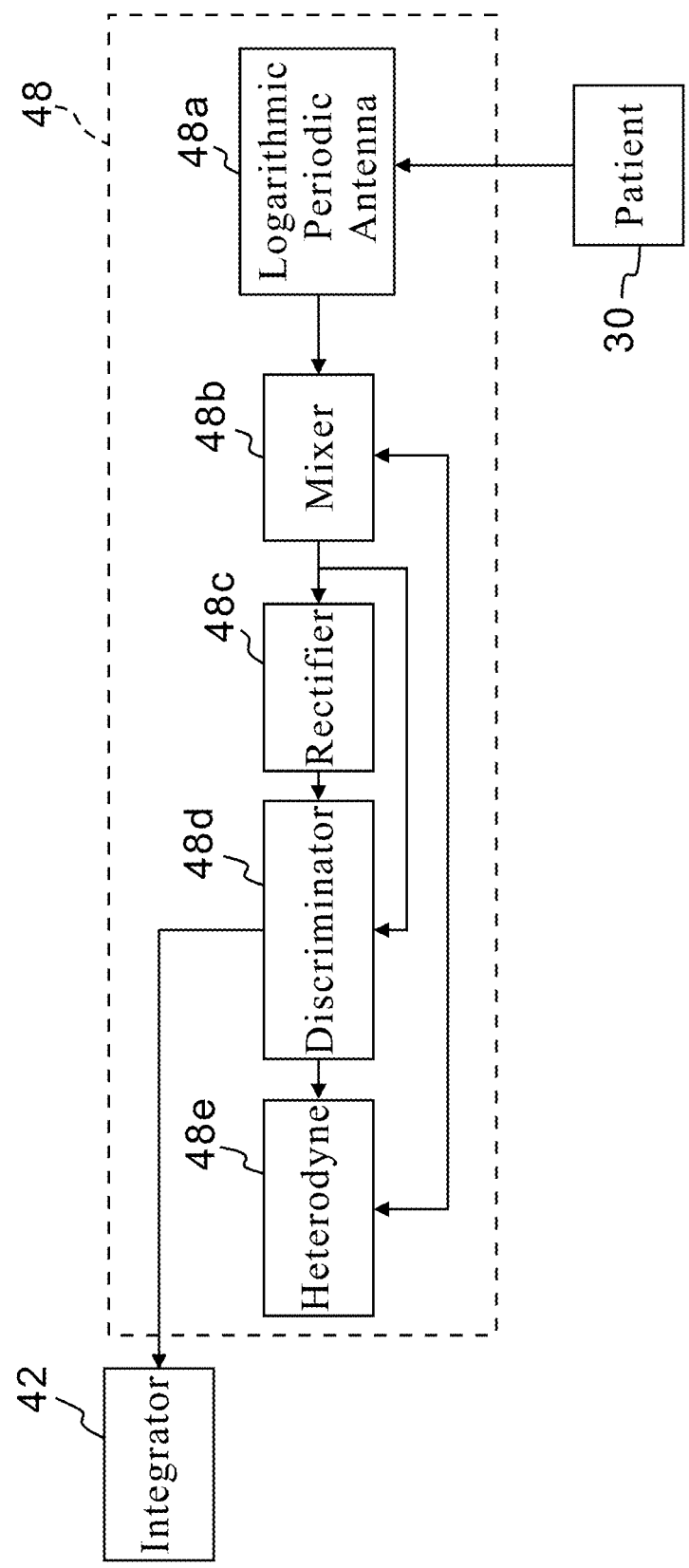
FIG. 2B is a block diagram of an embodiment of a detector channel.

Refer to FIG. 2B. FIG. 2B is a block diagram of an embodiment of a detector channel. In an embodiment, the detector channel 48 includes: an antenna such as a logarithmic periodic antenna 48a or other suitable antenna, a mixer 48b, a rectifier 48c, a discriminator 48d, and a heterodyne 48e.

The main function of the trigger sensor 40 is to sense the biofeedback signal and process it accurately. The stimulus signals (also called "information code") provided by the central processing and telemetry unit 10 pass through the biofeedback signal combined by the two loops of the operation unit 20 and the patient 30. The trigger sensor 40 receives the response, converts it into a digital signal and sends it back to the central processing and telemetry unit 10. The sensing element 41 is based on receiving, for example, the patient's biofeedback signal (0-150 Hz). A power supply 49 is used to provide a stable direct current to power the element. This current is adjustable and can be fine-tuned individually in the process outside the device.

The current source 43 includes a power amplifier and a regulating element (e.g., a bipolar transistor with a low noise factor) capable of providing a constant current level that is not affected by the fluctuation of the power supply voltage in order to avoid influence on the device due to the sensitivity to external interference.

The trigger sensor 40 is non-invasive and capable of noise processing. The noise processing takes the loop signal of the second biofeedback loop as the reference, obtains the information signal from the sensing element 41, and obtains the result through the amplification phase composed of the differential amplifier 44 and the amplifier 45. The signal is amplified, for example, the total amplification coefficient is about 30 dB. The sensing element 41 is simultaneously affected by interference and random interference such as from static electromagnetic fields. To eliminate this random interference, a precision differential amplifier 44 is used as the first stage of amplification. Where the signal voltage from the sensing element 41 is fed to one input of the differential amplifier 44, while the other input of the sensing element 41 is fed through the integrator 42 to provide the same voltage. As a result, while filtering out noise signals, only useful interference signals are allowed to pass through the next amplification stage in the amplifier 45. Any appropriate known amplifier can be used as an amplifier 45. The differential amplifier 44 removes the noise and performs primary signal phase and signal amplification after deducting the reference signal (noise) of the second biofeedback loop from the first biofeedback loop, and the amplifier 45 continues to amplify the signal to an appropriate coefficient, such as 30 dB. Of course, the implementation of the present invention is not limited by the above examples.

The comparator 46 is designed to convert an analog signal from the amplifier 45 into a series of pulses, such as in an A-D converter, which are then transmitted to a current decoupling unit 47 for further conversion.

The need for a current decoupling unit 47 depends on the presence of a random fluctuating electromagnetic noise field in the power supply line of the device according to the invention (such as an integral electronic device of a terahertz field effect non-invasive biofeedback diagnosis system) and other nearby electrical devices. The device according to the present invention can be designed to separate the alternating current (AC) component from the direct current (DC), and according to the embodiments of the present invention, the electromagnetic noise interference factors mentioned above have been controlled in the noise processing described above by subtracting the second biofeedback loop from the first biofeedback loop.

The detector channel 48 is, for example, configured as a high-sensitivity signal receiving unit to achieve a high-sensitivity reception of the biofeedback signal of the patient 30 to ensure that the sensing element 41 can obtain a signal of appropriate intensity. Biofeedback signals are known to be within the range of radio wave transmission of human biological proteins, cells, tissues and organs. In one embodiment, the receiving element is made of a logarithmic periodic antenna 48a with a multi-turn spiral conical design to ensure a narrow receiving direction but a wide transmission frequency range.

The mixer 48b is preferably mounted directly on the logarithmic periodic antenna 48a, for example, comprising a series of diodes to which the heterodyne 48e provides voltage. This heterodyne is usually a sinusoidal voltage generator and is widely used in radio receivers. It is tunable simultaneously with the tuning of the oscillating circuit of the receiver connected to the antenna. This allows the stationary value of the difference between the received signal and the frequency of the heterodyne signal to be marked at any position set by the radio receiver.

The rectifier 48c is designed to separate the low frequency phase interference signal from the useful signal and feed the signal into the discriminator 48d. The discriminator 48d subtracts its original background signal from the acquired signal to obtain a pure voltage pulse signal. This voltage pulse is then fed back to the integrator 42 and further to the current source 43, which changes the current numerical level of the current and changes the power current of the sensing element 41. Such fluctuations in the current of the sensing element 41 ultimately affect the frequency spectrum of its operation and the frequency range of the useful signal resulting therefrom.

Examples of the functions of the diagnosis system of the present invention are as follows. At the beginning of the test sequence, the central processing and telemetry unit 10 generates a stimulus signal (information code) as a stimulus signal of electromagnetic, radio, audio, optical signal, skin potential, vision, olfaction, or taste according to the evaluated diagnostic properties. These signals or stimuli affect the biomolecule receptor of the patient 30 to transform it into a highly sensitive and reactive state, thereby increasing the biofeedback strength between the patient 30; at the same time, the operation unit 20 converts the stimulus signal and environmental noise into a reference standard point signal. The action of the terahertz wave source field unit 50 has its impact on the patient 30. The terahertz electromagnetic spectrum is used to trigger the rotation and vibration energy of biomolecules to generate valuable biomolecular feedback signals. Through the sensing and accurate signal processing of the trigger sensor 40, the signals are transmitted back to the central processing and telemetry unit 10 for clinical analysis to complete the overall diagnosis system.

TABLE 1

Examples of operations

| | Peripheral Devices | | |
|---|---|---|---|
| Sequence | Magnetic Induction Coils Electromagnetic Impulses Frequency of Coil Interruptions | Video Monitor Stimuli Color Visual | Stereo Headsets Sound Audio (music notes) |
| 1 | 0-16.7 Hz | Dark Maroon | DO |
| 2 | 16.7-33.4 Hz | Red | RE |
| 3 | 33.4-50.1 Hz | Orange | MI |
| 4 | 50.1-66.8 Hz | Yellow | FA |
| 5 | 66.8-83.5 Hz | Green | FA-Dies |
| 6 | 83.5-100.3 Hz | Light Blue | SOL |
| 7 | 100.3-117 Hz | Blue | LA |
| 8 | 117-133.7 Hz | Violet | SI |
| 9 | 133.7-150 Hz | Dark Violet | DO |

Table 1 gives an example of various stimulus signals generated by the central processing and telemetry unit 10 of the diagnosis system of the present invention. The starting time of each stimulus signal sequence is coordinated with each other and with the start of trigger sensor 40 and terahertz wave source field unit 50, so that the operation unit 20 and patient 30 receive the stimulus signals and form a biofeedback loop in the system. In addition, in the embodiments as shown in Table 1, magnetic induction coils, displays, and headphones (or speakers) are used as peripheral devices, and electromagnetic, video, and audio signals are sent to the patient 30 and the operation unit 20 as stimulus signals (information codes).

As a result, the central processing and telemetry unit accumulates feedback signals from the operating unit 20 and the patient 30, thus forming a database that includes responses to each series of individual stimuli. The human body is a complex resonance system, and all organs and tissues have their own specific biomolecular resonance frequencies, which generally range from 0 to 150 Hz, such as four basic brain waves: Delta 0-4 Hz; THETA 4-7 Hz; Alpha 8-13 Hz; and Beta 13-40 Hz.

For example, studies conducted by the inventor have shown that when the interference frequency of electromagnetic pulses approaches the Theta ($\theta$) rhythm of a patient's brain wave, the patient's effect on the trigger sensor is more reproducible. This frequency tends to increase and decrease with the patient's health. In fact, the relationship between this frequency bias and the specific pathological conditions of certain body systems, specific organs, and even isolated cells and chromosomal segments is well established.

This relationship allows for special diagnosis of various pathological conditions. Examples include, diagnosis of spinal disc herniation, distant metastasis of various cancer tumors, fractures and general trauma, vascular thrombosis, acute and chronic hepatitis, cirrhosis, and diagnosis of various other pathological conditions. It should be emphasized that this diagnosis can be made using biofeedback signals of brain functions, independent of the influence of patient's ideation.

The device of the present invention collects digital standards of biomolecular tissue organs obtained by trigger sensors using available feature libraries previously collected from normal volunteers. Such comparative analysis can determine the pathological degree of biomolecular organs and organs and the state of disease development.

The following classification methods developed by the inventor can further characterize the disease state:

Level 0—Ideal correlation between the digital criteria of the organs and tissues being evaluated for biomolecules and the normal criteria in the archives. For example, human egg cells begin the division process;

Level 1—Tissue of healthy prenatal embryos (without any physical function or toxins);

Level 2—Tissue of healthy newborns at the early stage of birth, and in vitro, tissue function is in the initial stage;

Level 3—Functionally active tissue, free of toxins;

Level 4—Functionally impaired tissues where toxin accumulation is just beginning;

Level 5—Organic changes in tissues where toxins accumulate within tissue cells and actively limit their function; and Level 6—Extreme and irreversible state of organ damage and overall tissue imbalance.

For example, the trigger sensor according to the device of the present invention is used to collect embryos and biomolecular tissue organs of the six feature library levels mentioned above clinically, and to establish digital standards for biomolecular tissue organs, in order to be easily identifiable as: level 1 (hexagonal beige), Level 2 (hexagonal yellow), Level 3 (regular triangular orange), level 4 (inverted triangular red), level 5 (diamond brown), level 6 (square black), etc., as shape and color discrimination management.

Figure 3:
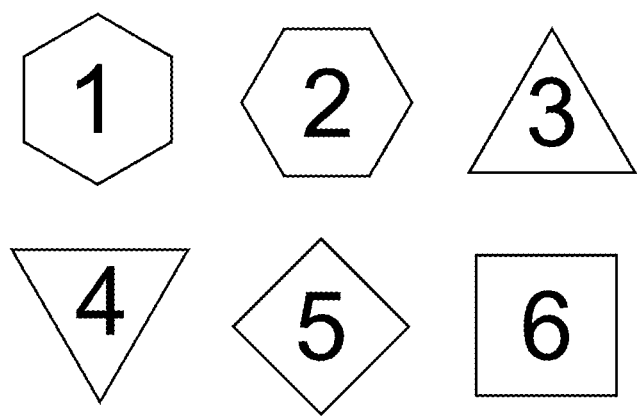
FIG. 3 is a schematic diagram of an embodiment of symbols that characterize the disease state.

For example, software can be implemented using computing devices or computers to display the detected biomolecular tissues and organs using images, and symbols of geometry are used to represent disease states on the images of organs for the purpose of assisted diagnosis. For example, FIG. 3 shows a schematic illustration of an embodiment of symbols that characterize a disease state, in which only geometric symbols are used in a simplified form to represent levels 1 to 6 without displaying color. Of course, the method of implementation of the present invention is not limited by the above examples, and the disease state can be characterized by any suitable way, or the series of disease states can be increased or decreased as needed.

Figure 4:
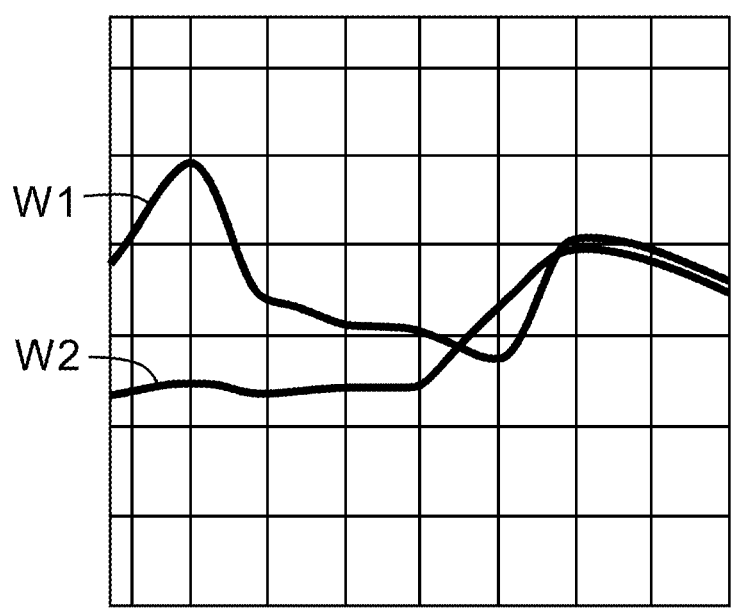
FIG. 4 is a schematic diagram of an embodiment of a scanned waveform signal.

Some of the research results obtained by applying the terahertz field effect non-invasive biofeedback diagnosis system in the embodiments of the present invention are illustrated by examples. For example, a terahertz field effect non-invasive biofeedback diagnosis system is used to scan the whole brain base for cerebrovascular biomolecules, to confirm the location of the blood vessels at the bottom of the brain under the terahertz wave source field, and then to turn off the terahertz wave source field for scanning at frequencies from 0 to 150 hertz. The terahertz field effect non-invasive biofeedback diagnosis system can obtain the first scanning waveform (as shown in the scanning diagram of FIG. 4, the waveform represented by W1), then, after turning on the terahertz waveform source field, another 0-150 Hz scan is performed, and the second scanning waveform (represented by W2 in the scanning diagram of FIG. 4) can be obtained by the terahertz field effect non-invasive biofeedback diagnosis system. Thus, the digital standard signal of cerebrovascular biomolecular tissue and organs, the first scanning waveform signal and the second scanning waveform can be established according to the digital standard signal of cerebrovascular biomolecular tissue and organs. The signal is compared individually, and then the difference between the digital standard signal of cerebrovascular biomolecular organs and the signal of the second and first scanning waveforms is compared to finally confirm which level of the cerebrovascular biofeedback signal is, level 1-6.

Figure 5:
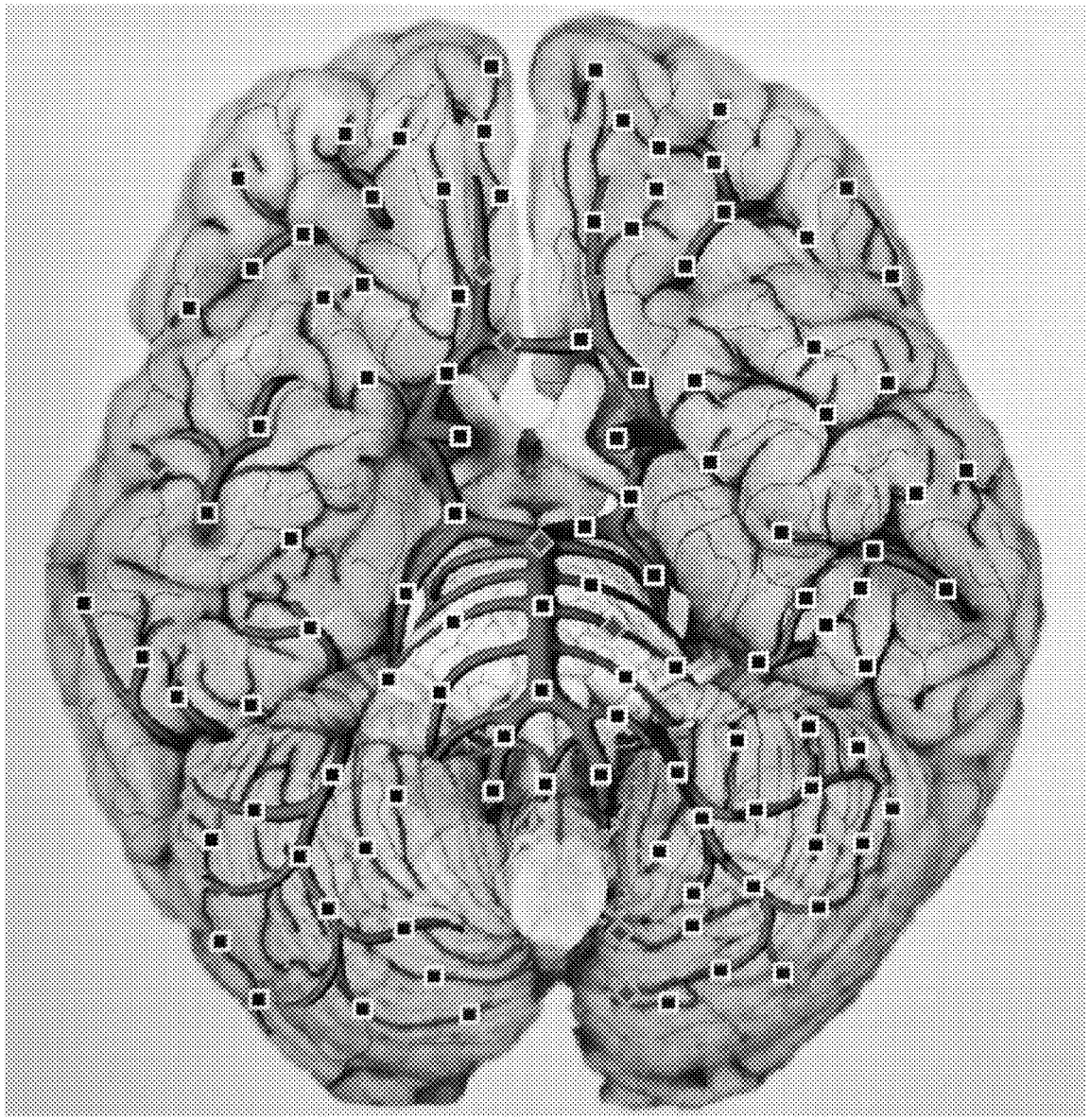
FIG. 5 is a schematic diagram of an example in which a brain vascular biomolecular scan is performed at the bottom of the brain and the disease state is characterized by the symbols shown in FIG. 3.

The above comparison can be realized on a terahertz field effect non-invasive biofeedback diagnosis system, for example, by means of an operation device, software, etc. to automate the comparison, or displayed on a display for researchers to judge. Please refer to FIG. 5, which is a schematic illustration of an example of performing a cerebrovascular biomolecular scan of the bottom of the brain and using the symbols shown in FIG. 3 to characterize the disease state. From the brain sampling point scan in the embodiment of FIG. 5, it can be seen that the biofeedback signal results are in levels 5 and 6.

Figure 6:
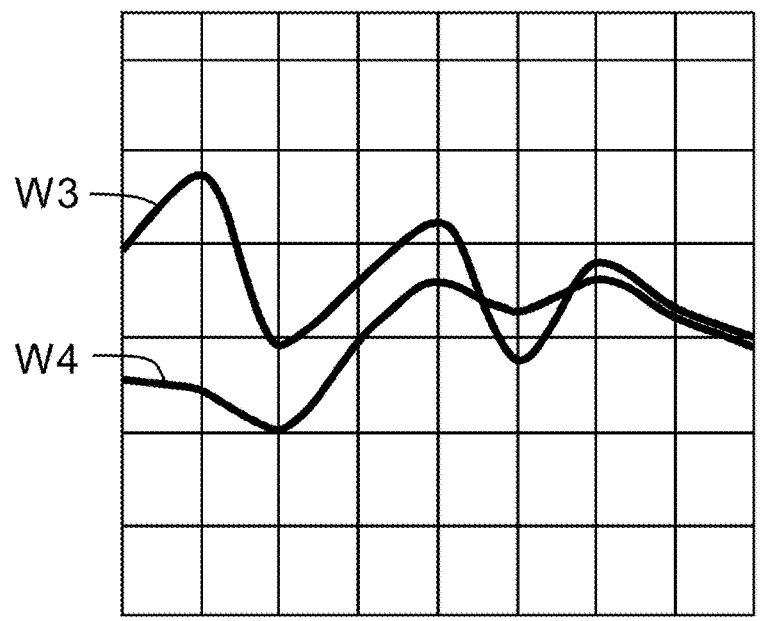
FIG. 6 is a schematic diagram of another embodiment of a scanned waveform signal.
Figure 7:
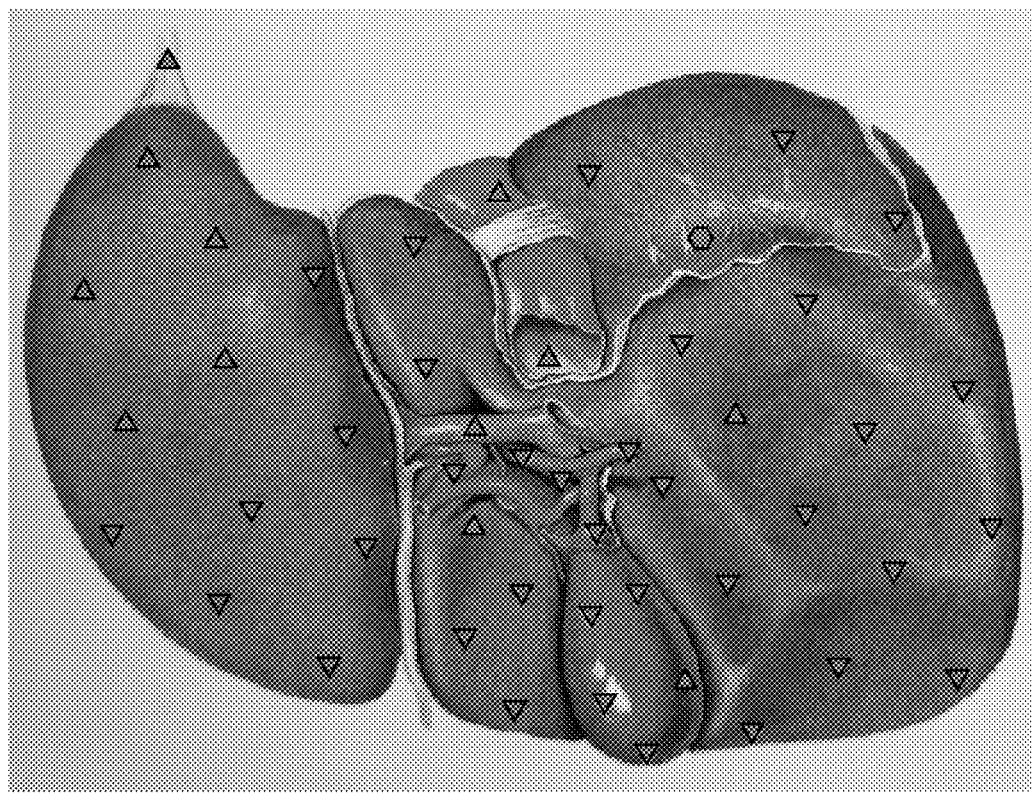
FIG. 7 is a schematic illustration of an example of molecular scanning of liver cells and characterizing a disease state using the symbols shown in FIG. 3.

In another example, a molecular scan of a liver cell is performed. As described above, a terahertz field effect non-invasive biofeedback diagnosis system is used to perform a similar scanning mode as in the previous example, and the first scanning waveform signal and the second scanning waveform signal are compared according to the digital standard signal of the biomolecular tissue and organ of the hepatocyte. For example, in the scanning diagram of FIG. 6, W3 and W4 represent the first scanning waveform and the second scanning waveform in the present example, respectively. Refer to FIG. 7, which is a schematic illustration of an example of molecular scanning of liver cells and characterizing the disease state using the symbols shown in FIG. 3. From the liver sampling point scan diagram in the embodiment of FIG. 7, it is confirmed that the hepatocyte biofeedback signal is in levels 2, 3 and 4. In the embodiments of the present invention, the biofeedback signal obtained by the non-invasive biofeedback diagnosis system utilizing terahertz field effect is quite sensitive, and can have obvious signal feedback before the biomolecule has entered pathological damage or damage (such as level 1-3). The quantification result of the biofeedback signal can be used as a reference for clinical diagnosis.

In summary, a biofeedback diagnosis system provided in the embodiments of the present invention provides a series of stimulus signals for a patient, and has reference baseline standard points to collect valuable biofeedback signals, thereby overcoming the bottlenecks and shortcomings of the prior art. The biofeedback diagnosis system can process the two-loop biofeedback diagnosis system from the patient and the operation unit. The reference standard point signal provided by the operation unit and the same path of the patient biofeedback signal are processed, analyzed and compared with the trigger sensor to obtain a more accurate signal.

The above description is only an example of the present invention and is not intended to limit the patent scope of the present invention.

While the present disclosure has been described by means of specific embodiments, numerous modifications and variations could be made thereto by those skilled in the art without departing from the scope and spirit of the present disclosure set forth in the claims.

What is claimed is:

1. A terahertz field effect non-invasive biofeedback diagnosis system, comprising:
  a central processing and telemetry unit;
  a trigger sensor, the trigger sensor being non-invasive and capable of noise processing; and
  a terahertz wave source field unit coupled to and in collaboration with the central processing and telemetry unit for triggering rotation and vibration energy of a patient's biomolecule using terahertz electromagnetic spectrum;
  wherein the central processing and telemetry unit is used to generate a predetermined series of stimulus signals, and simultaneously transmit the stimulus signals to an operation unit and the patient, thereby forming a plurality of biofeedback loops comprising:
- a first biofeedback loop, the first biofeedback loop comprising the central processing and telemetry unit transmitting the stimulus signals to the patient, the trigger sensor being used for remotely detecting a biofeedback signal of the biomolecule of the patient, and the trigger sensor further processing the biofeedback signal to obtain a processed feedback signal and transmitting the processed feedback signal back to the central processing and telemetry unit; and
- a second biofeedback loop, the second biofeedback loop comprising the central processing and telemetry unit transmitting the stimulus signals to the operation unit, the operation unit converting the stimulus signals into a reference baseline standard point signal, the trigger sensor receiving the reference baseline standard point signal and sending the processed feedback signal back to the central processing and telemetry unit to form a reference loop that provides a reference value for accurately calculating phase and intensity of the processed feedback signal by excluding the patient within the second biofeedback loop,
- wherein the central processing and telemetry unit is configured to control the turning on or off of the terahertz wave source field unit by a control signal and wherein the terahertz wave source field unit triggers the biofeedback signal of the biomolecule of the patient
wherein the central processing and telemetry unit is configured to instruct the terahertz wave source field unit to generate different frequency band signals.

2. The terahertz field effect non-invasive biofeedback diagnosis system according to claim 1, wherein the central processing and telemetry unit comprises:
- a stimulus signal generation module for generating the predetermined series of stimulus signals; and
- a stimulus signal transmission device, coupled to the stimulus signal generation module, for transmitting the predetermined series of stimulus signals to the operation unit and the patient simultaneously.

3. The terahertz field effect non-invasive biofeedback diagnosis system according to claim 1, wherein the stimulus signals include at least one of a magnetic, electromagnetic, audio and visual stimulation signal or a combination thereof.

4. The terahertz field effect non-invasive biofeedback diagnosis system according to claim 1, wherein the trigger sensor further comprises a detector channel equipped with a logarithmic periodic antenna to enhance reception of the biofeedback signal.

5. The terahertz field effect non-invasive biofeedback diagnosis system according to claim 4, wherein the logarithmic periodic antenna is a multi-turn conical helical antenna for receiving short waves in the range of 450 MHz to 6000 MHz.

6. The terahertz field effect non-invasive biofeedback diagnosis system according to claim 4, wherein the detector channel also comprises a mixer, a rectifier, a discriminator, and a heterodyne;
- wherein the logarithmic periodic antenna is coupled to the mixer; the mixer is coupled to the rectifier, the discriminator, and the heterodyne; and the rectifier is coupled to the discriminator; thereby enhancing the reception of the biofeedback signal.

7. The terahertz field effect non-invasive biofeedback diagnosis system according to claim 4, wherein the trigger sensor further comprises a sensing element, an integrator, a differential amplifier, an amplifier, and a comparator;
- wherein the sensing element is coupled to the integrator and the differential amplifier; the differential amplifier is coupled to the amplifier; and the amplifier is coupled to the comparator; enabling the trigger sensor to analyze and compare the frequency, phase, and timing of the biofeedback signal.

8. The terahertz field effect non-invasive biofeedback diagnosis system according to claim 1, wherein the terahertz wave source field unit comprises a split-ring resonator (SRR) structure to enhance the terahertz field local electromagnetic response, thereby enhancing absorption sensitivity of the terahertz spectrum corresponding to various biomolecules.

9. The terahertz field effect non-invasive biofeedback diagnosis system according to claim 1, wherein the terahertz wave source field unit generates terahertz waves by way of semiconductor instantaneous current generation, accelerated electronic generation, photorectification generation, semiconductor photoconductivity generation, nonlinear differential frequency generation, thermal radiation generation, high energy accelerator generation, thermal radiation generation, or Fourier transform infrared spectroscopy.

* * * * *